United States Patent [19]

Morgan et al.

[11] 4,117,017
[45] Sep. 26, 1978

[54] PROCESS FOR PREPARATION OF THIOLS USING A BENZOPINACOL INITIATOR

[75] Inventors: Charles Robert Morgan, Brookeville; Richard Wayne Bush, Columbia, both of Md.

[73] Assignee: W. R. Grace & Co., New York, N.Y.

[21] Appl. No.: 788,161

[22] Filed: Apr. 18, 1977

[51] Int. Cl.² .......................................... C07C 149/00
[52] U.S. Cl. ........................... 260/609 R; 204/159.22; 260/609 D; 260/455 R; 528/376; 560/26
[58] Field of Search .......... 260/609 R, 609 F, 471 C, 260/455 R, 609 D; 560/26

[56] References Cited

U.S. PATENT DOCUMENTS

| | | | |
|---|---|---|---|
| 2,398,479 | 4/1946 | Vaughan et al. | 204/163 |
| 2,411,983 | 12/1946 | Vaughan et al. | 204/163 |
| 2,551,813 | 5/1951 | Pinkney | 260/609 |
| 3,050,452 | 8/1962 | Louthan | 204/162 |
| 3,270,063 | 8/1966 | Fath et al. | 260/609 |
| 3,522,313 | 7/1970 | Reece et al. | 260/609 R |
| 3,607,945 | 9/1971 | Reece | 260/609 R |
| 3,823,191 | 7/1974 | Dighe | 260/609 R |

OTHER PUBLICATIONS

D. Braun et al., Chemical Abstracts, 71:3671w, (1969).

*Primary Examiner*—Lewis Gotts
*Assistant Examiner*—Molly C. Eakin
*Attorney, Agent, or Firm*—Richard P. Plunkett; William W. McDowell, Jr.

[57] ABSTRACT

This invention relates to a process for preparing thiols and polythiols by the addition of a thiolcarboxylic acid, e.g., thiolacetic acid, to ethylenically unsaturated compounds in the presence of an initiator comprising a pinacol of the general formula:

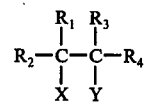

wherein $R_1$ and $R_3$ are members independently selected from the group consisting of substituted and unsubstituted aromatic radicals, $R_2$ and $R_4$ are members independently selected from the group consisting of substituted and unsubstituted aliphatic and aromatic radicals and X and Y are members independently selected from the group consisting of hydroxyl, alkoxy and aryloxy to obtain a thiol ester which is thereafter hydrolyzed to yield the corresponding thiol.

3 Claims, No Drawings

PROCESS FOR PREPARATION OF THIOLS USING A BENZOPINACOL INITIATOR

This invention relates to a process for preparing thiols and polythiols by the addition of a thiolcarboxylic acid, e.g., thiolacetic acid, to ethylenically unsaturated compounds in the presence of a pinacol initiator to form thiol esters which are hydrolyzed to yield thiols.

Polythiols are especially useful in combination with polyenes to form cured polythioethers. See U.S. Pat. No. 3,661,744. Additionally, primary thiols are useful as chain transfer agents to control the chain lengths of synthetic rubbers and other well known polymers.

In the chief commercial method of forming thiols an olefin is reacted directly with $H_2S$. In another method of forming thiols an alcohol corresponding in structure to the desired thiol is used. In this method the alcohol is converted to the alkyl chloride which is then reacted with sodium hydrosulfide to form the thiol.

A major problem with the first method is the formation of sulfides as by-products. This happens due to the fact that the thiol formed is able to react further with unreacted olefin in competition with $H_2S$, thereby forming a sulfide-containing product from which thiol cannot be readily regenerated. Since the reaction rate of this undesired reaction is considerable, a good percentage of the thiol formed by the desired reaction is lost in forming the undesired sulfide-containing compound. In the second method disulfides are formed as an undesirable by-product.

It is known from U.S. Pat. No. 3,270,063 to form primary mercaptans from the reaction of a thiol acid with olefinnically unsaturated compounds in the presence of an azo-catalyst. It is also known to make terminal thiols (primary mercaptans) by addition of hydrogen sulfide to 1-olefins under free radical conditions. Such a method using ultraviolet radiation is set out in U.S. Pat. No. 2,398,479. The reaction rate of this system has been enhanced by the use of promoters or sensitizers as shown in U.S. Pat. Nos. 2,411,983 and 3,050,452. Azo-nitriles as shown by U.S. Pat. No. 2,551,813 have also been used to initiate this reaction. Additionally, heat or peroxide initiators have also been used. The drawback when using light energy to initiate the reaction is that complex U.V. equipment is required and the amount of product obtained is limited to small quantities. When thiolcarboxylic acids are used with light energy or peroxides, the reaction rate depends greatly on the purity of the reagent and the reaction is often uncontrollable. A further drawback with peroxides is that they are highly hazardous.

It has been found that all the aforesaid disadvantages are overcome when benzopinacol and substituted benzopinacol are used to initiate the addition of a thiolcarboxylic acid to an ethylenically unsaturated compound.

Thus, it has now been discovered in the instant invention that primary thiols may be prepared from ethylenically unsaturated compounds under normal processing conditions involving only atmospheric pressure, normal temperatures and without extensive sulfide formation by the addition of thiolcarboxylic acids to double bonds in ethylenically unsaturated compounds in the presence of an initiator comprising benzopinacol or substituted benzopinacol.

Accordingly, this invention relates to a process for reacting ethylenically unsaturated compounds with a thiolcarboxylic acid of the formula

wherein R is an alkyl or aryl group containing 1–6 carbon atoms in the presence of an initiator comprising a pinacol of the general formula:

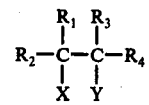

wherein $R_1$ and $R_3$ are members independently selected from the group consisting of substituted and unsubstituted aromatic radicals, $R_2$ and $R_4$ are members independently selected from the group consisting of substituted and unsubstituted aliphatic and aromatic radicals and X and Y are members independently selected from the group consisting of hydroxyl, alkoxy and aryloxy at a temperature of at least 50° C, preferably 80°–150° C, for a time sufficient to form a thiol ester and, thereafter, hydrolyzing the thiol ester so formed to form a thiol.

As used herein, the term "ethylenically unsaturated compound" means compounds having terminal or pendant ethylenic unsaturation or any combination thereof. Also, as used herein, the thiol product means primary thiols or polythiols.

Any compound having terminal or pendant ethylenic unsaturation or any combination thereof including those containing more than one carbon-to-carbon double bond is operable in the instant invention to form thiols and polythiols herein. In addition, other functional groups such as esters, ethers, ketones, halides, amides and hydroxyls can also be present in the ethylenically unsaturated compound. The hydrocarbon moieties of these compounds may be straight-chained or branched, aromatic, aliphatic or cycloaliphatic.

The thiolcarboxylic acid used in the invention may be employed per se or may be prepared in situ. Typical examples of operable thiolcarboxylic acids herein include, but are not limited to, thiolacetic acid, thiolpropionic acid, thiolbutyric acid, thiolbenzoic acid and the like. One method of in situ preparation comprises sparging $H_2S$ at or slightly above atmospheric pressure into an alkyl or aryl anhydride containing 1–6 carbon atoms in the presence of a basic or acidic catalyst. The advantage of this process is that the thiol acid formed need not be purified for subsequent reactions but may be used in a mixture with the carboxylic acid formed as a coproduct. For the in situ preparation of the thiol acid both basic and acidic catalysts are operable. Examples of basic catalysts operable in the system include, but are not limited to, potassium hydroxide, sodium hydroxide, sodium carbonate, potassium carbonate, sodium acetate or organic bases such as triethylamine, pyridine, dimethylaniline or other tertiary amines. Basic catalysts because of their better rate of hydrogen sulfide absorption and higher yields of thiolcarboxylic acid are preferred over acidic catalysts such as sulfuric acid, toluenesulfonic acid and the like. When basic catalysts are used, it is necessary to neutralize the catalyst prior to use of the thiolcarboxylic acid for further reaction. Neutralization can be carried out with phosphoric or toluenesulfuric acids to form the corresponding salts which are inert to the subsequent reaction. Additionally, if desired, pure thiolcarboxylic acid may be employed as a reactant.

The thiolcarboxylic acid in the mixture is then reacted with the desired ethylenically unsaturated compound in the presence of benzopinacol at slightly elevated temperatures, i.e., at least 50° C, preferably 80°–150° C, to form the corresponding thiol ester. The thiol ester is then hydrolyzed with an alkali metal hydroxide to form the alkylate salt and the corresponding desired thiol or alkali sulfide. The reaction mixture is then acidified to generate the thiol, optionally extracted with a solvent for the thiol and washed. The thiol is separated from the solvent by distillation. By this method the thiol is relatively easily obtained in substantially pure form.

The reaction of the instant invention is initiated by a substituted or unsubstituted pinacol of the general formula:

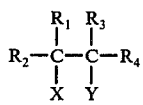

wherein $R_1$ and $R_3$ are the same or different substituted or unsubstituted aromatic radicals, $R_2$ and $R_4$ are substituted or unsubstituted aliphatic or aromatic radicals and X and Y which may be the same or different are hydroxyl, alkoxy or aryloxy.

Preferred pinacols are those wherein $R_1$, $R_2$, $R_3$, and $R_4$ are aromatic radicals, especially phenyl radical and X and Y are hydroxyl.

Examples of this class of compounds include but are not limited to benzopinacol, 4,4'-dichlorobenzopinacol, 4,4'-dibromobenzopinacol, 4,4'-diiodobenzopinacol, 4,4',4'',4'''-tetrachlorobenzopinacol, 2,4–2',4'-tetrachlorobenzopinacol, 4,4'-dimethylbenzopinacol, 3,3'-dimethylbenzopinacol, 2,2'-dimethylbenzopinacol, 3,4–3',4'-tetramethylbenzopinacol, 4,4'-dimethoxybenzopinacol, 4,4',4'',4'''-tetramethoxybenzopinacol, 4,4'-diphenylbenzopinacol, 4,4'-dichloro-4'',4'''-dimethylbenzopinacol, 4,4'-dimethyl-4'',4'''-diphenylbenzopinacol, xanthonpinacol, fluorenonepinacol, acetophenonepinacol, 4,4'-dimethylacetophenone-pinacol, 4,4'-dichloro-acetophenonepinacol, 1,1,2-triphenyl-propane-1,2-diol, 1,2,3,4-tetraphenylbutane-2,3-diol, 1,2-diphenylcyclobutane-1,2-diol, propiophenone-pinacol, 4,4'-dimethylpropiophenone-pinacol, 2,2'-ethyl-3,3'-dimethoxy-propiophenone-pinacol, 1,1,1,4,4,4-hexafluoro-2,3-diphenyl-butane-2,3-diol.

As further initiating compounds according to the present invention, there may be mentioned: benzopinacolmono methylether, benzopinacol-mono-phenylether, benzopinacol-monoisopropyl ether, benzopinacol-monoisobutyl ether, benzopinacol-mono(diethoxy methyl) ether and the like.

The pinacol is added to the composition in amounts ranging from 0.01–5% preferably 0.1–3% by weight based on the weight of the ethylenically unsaturated compound and the thiolcarboxylic acid.

If desired, the reaction can be carried out in a solvent. Operable solvents should be free of ethylenic unsaturation and have a boiling point higher than the reaction temperature. Such solvents include, but are not limited to, aromatic hydrocarbons, e.g., benzene, toluene, xylene and saturated hydrocarbons such as hexane, cyclohexane, heptane and the like.

Carrying out the instant invention, the preferred method of operation is to add the benzopinacol initiator to the ethylenically unsaturated compound which is then added to the thiolcarboxylic acid which has been preheated to the desired reaction temperature, either alone or admixed with a solvent. Heating is continued until the corresponding thiol ester is formed. The thiol ester is then hydrolyzed with an alkali metal hydroxide under refluxing conditions for periods ranging from 30 minutes up to 8 hours. The mixture is cooled, then acidified with hydrochloric or other mineral acid. The organic layer is separated and the aqueous layer is extracted with an organic solvent, e.g., benzene, and the combined organic layers are washed successively with a weak alkaline solution, e.g., 5% sodium carbonate, followed by a dilute acid wash, e.g., 5% hydrochloric acid and finally a water wash. The solution is then dried, e.g., over anhydrous magnesium sulfate, and the thiol and solvent are separated by distillation.

The following examples will aid to explain but specifically not limit the instant invention. Unless otherwise noted, all parts and percentages are by weight.

EXAMPLE 1

1gram mole of a commercially available 80–20 percent isomer mixture of tolylene-2,4-diisocyanate and tolylene-2,6-diisocyanate, respectively, was charged to a resin kettle equipped with a condenser, stirrer, thermometer and gas inlet and outlet. 2 gram-moles of the diallyl ether of trimethylolpropane was slowly added to the kettle. After the addition was complete, 0.5 grams of dibutyl tin dilaurate as a catalyst was added to the kettle and the reaction was continued for 30 minutes at 70° C under nitrogen. The thus formed allyl terminated liquid prepolymer of the formula:

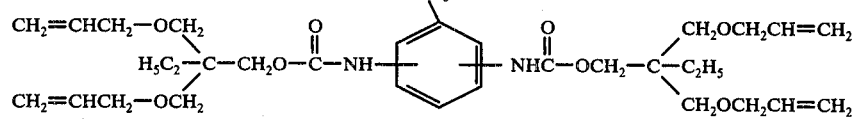

will hereinafter be referred to as Prepolymer A.

EXAMPLE 2

A mixture of 148.6 g of Prepolymer A from Example 1 containing 6.73 mmoles of unsaturation per gram, 83.6 g (1.1 moles) of thiolacetic acid and 1.2 g of benzopinacol was heated for 2 hours at 90°–100° C in a 1 liter round bottom flask. To the solution was added 500 ml of 5.0 M sodium hydroxide, and the mixture was heated at reflux for 2 hours. The mixture was cooled and acidified with 6N hydrochloric acid. The organic layer was separated, the aqueous layer was extracted with benzene and the combined organic layers were washed successively with 5% sodium bicarbonate, 5% hydrochloric acid and water. The solution was dried over anhydrous magnesium sulfate and the benzene was removed by distillation. The product was 142 g of a liquid containing 4.0 meq SH/g, compared to a theoretical yield of 183 g containing 5.46 meq SH/g.

EXAMPLE 3

A solution of 2.3 g of benzopinacol in 111.4 g of commercially available trimethylopropane diallyl ether (containing 8.98 mmoles of unsaturation per gram) was gradually added to 114 g (1.5 moles) of refluxing thiolacetic acid in a 2-liter round bottom flask and heating at 90°–100° C was continued for 2 hours after addition. To the solution was added 500 ml of 7.0 M sodium hydroxide, and the mixture was refluxed for 2 hours, then worked up as in Example 2. The product was 122 g of a liquid containing 6.51 meq SH/g compared to a theoretical yield of 145 g containing 6.88 meq SH/g.

EXAMPLE 4

Into a 5 liter three-necked flask fitted with condenser and addition funnel was placed a solution of 650 g (16.25 equivalents) of sodium hydroxide in 650 ml of water. To this was added 272 g (two moles) of pentaerythritol. This mixture was stirred by means of a magnetic bar and heated to 70° C. Then 1936 g (1385 ml 16 moles) of allyl bromide was added over an 8-hour period at such a rate that the temperature stayed between 70° C and 80° C. Following this, heating was resumed, keeping the temperature at 80°–82° C for an additional four hours. Volatile materials were removed by distillation at atmospheric pressure until the temperature of the condensing vapor reached 98° C.

One liter of water was added to the hot residue (to prevent crystallization of the salts). The product was cooled to room temperature and the layers were separated. The water layer was extracted twice with 300 ml portions of diethyl ether. The combined organic layers were dried over anhydrous magnesium sulfate and then distilled at atmospheric pressure to remove the diethyl ether. The triallyl ether of pentaerythritol product, i.e.

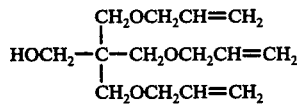

weighed 451 g (88% conversion). The infrared and NMR spectra were those expected for the triallyl ether of pentaerythritol. The triallyl ether of pentaerythritol product had a boiling range of 120°–121° C at 1 mm, $n_D^{24}$ 1.4625.

EXAMPLE 5

A solution of 1.7 g of benzopinacol in 86 g of pentaerythritol triallyl ether from Example 4 (containing 11.63 mmoles of unsaturation per gram) was gradually added to 84 g (1.1 moles) of refluxing thiolacetic acid in a 1-liter round bottom flask, and heating at 90°–100° C continued for 2 hours after addition. To the solution was added 500 ml of 5.0 M sodium hydroxide, and the mixture was refluxed for 2 hours and worked up as in Example 2. The product was vacuum stripped at 200° C for 2 hours. The final product was 74 g of a liquid containing 6.69 meq SH/g, compared to a theoretical yield of 120 g containing 8.33 meq SH/g.

The following example shows how to form a cured polythioether from the polythiol herein formed in combination with a polyene and photosensitizer using U.V. radiation:

EXAMPLE 6

A mixture was made consisting of 25.46 g of Prepolymer A of Example 1, 24.54 g of a polythiol prepared substantially as in Example 5 (containing 6.98 meq SH/g), 0.5 g of benzophenone, 0.05 g pyrogallol and 0.01 g of phosphorous acid. The mixture was coated onto a glass plate to a thickness of approximately 0.03 inches and exposed for 3 minutes to U.V. light from a Ferro-Allied ultraviolet energy source module containing a 1440-watt 24-inch (60 watt/inch) GE H24T3 medium pressure mercury lamp in a parabolic reflector set to deliver an intensity of approximately 11 milliwatts/cm² of U.V. power in the 300–400 nanometer region. A solid cured polythioether film resulted.

We claim:

1. The process of forming a primary thiol which comprises reacting at a temperature in the range 50°–150° C an ethylenically unsaturated compound, said unsaturation being in the terminal or pendant position or a combination thereof, with a thiolcarboxylic acid of the general formula:

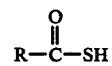

wherein R is phenyl or an alkyl radical containing 1–6 carbon atoms in the presence of 0.01–5% by weight of the ethylenically unsaturated compound and the thiolcarboxylic acid, of an initiator comprising a pinacol of the general formula:

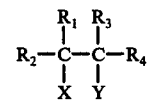

wherein $R_1$ and $R_3$ are aromatic radicals of the structure —$C_6H_4Z$, where Z is independently selected from the group consisting of H, Cl, Br, I, alkyl, aryl, and alkoxy; and $R_2$ and $R_4$ are members independently selected from the group consisting of $R_1$ and $R_3$ (as defined above), alkyl, aralkyl, alkoxyalkyl, haloalkyl and $R_2$ and $R_4$ together form a cycloalkyl group; and X and Y are members independently selected from the group consisting of hydroxyl, alkoxy and aryloxy to obtain a thiol ester and, thereafter, hydrolyzing said thiol ester with an alkali metal hydroxide to obtain the corresponding primary thiol.

2. The process of claim 1 wherein the thiolcarboxylic acid is thiolacetic acid.

3. The process of claim 1 wherein the pinacol is benzopinacol.

* * * * *